(12) United States Patent
Simpson

(10) Patent No.: US 6,342,074 B1
(45) Date of Patent: Jan. 29, 2002

(54) ANTERIOR LUMBAR INTERBODY FUSION IMPLANT AND METHOD FOR FUSING ADJACENT VERTEBRAE

(76) Inventor: Nathan S. Simpson, 2521 Glenn Hendren Dr., Suite 204, Liberty, MO (US) 64068

(*) Notice: Subject to any disclaimer, the term of this patent is extended or adjusted under 35 U.S.C. 154(b) by 0 days.

(21) Appl. No.: 09/557,481

(22) Filed: Apr. 24, 2000

Related U.S. Application Data

(60) Provisional application No. 60/131,900, filed on Apr. 30, 1999.

(51) Int. Cl.[7] ................................................. A61F 2/44
(52) U.S. Cl. .................................................... 623/17.11
(58) Field of Search ........................... 623/17.11, 17.15, 623/17.16

(56) References Cited

U.S. PATENT DOCUMENTS

| | | | |
|---|---|---|---|
| 3,426,364 A | 2/1969 | Lumb | 3/1 |
| 3,867,728 A | 2/1975 | Stubstad et al. | 3/1 |
| 4,349,921 A | 9/1982 | Kuntz | 3/1 |
| 4,599,086 A | 7/1986 | Doty | 623/17 |
| 4,743,256 A | 5/1988 | Brantigan | 623/17 |
| 4,874,389 A | 10/1989 | Downey | 623/17 |
| 4,892,545 A | 1/1990 | Day et al. | 623/17 |
| 4,904,261 A | 2/1990 | Dove et al. | 623/17 |
| 4,917,704 A | 4/1990 | Frey et al. | 623/17 |
| 4,955,908 A | 9/1990 | Frey et al. | 623/17 |
| 5,002,576 A | 3/1991 | Fuhrmann et al. | 623/17 |
| 5,035,716 A | 7/1991 | Downey | 623/17 |
| 5,123,926 A | 6/1992 | Pisharodi | 623/17 |
| 5,171,281 A | 12/1992 | Parsons et al. | 623/17 |
| 5,397,364 A | 3/1995 | Kozak et al. | 623/17 |
| 5,415,661 A | 5/1995 | Holmes | 606/69 |
| 5,458,638 A | 10/1995 | Kuslich et al. | 623/17 |
| 5,458,641 A | 10/1995 | Jimenez | 623/17 |
| 5,458,642 A | 10/1995 | Beer et al. | 623/17 |
| 5,458,643 A | 10/1995 | Oka et al. | 623/18 |
| 5,514,180 A | 5/1996 | Heggeness et al. | 623/17 |
| 5,522,899 A | 6/1996 | Michelson | 623/17 |
| 5,534,028 A | 7/1996 | Bao et al. | 623/17 |
| 5,545,229 A | 8/1996 | Parsons et al. | 623/17 |
| 5,556,431 A | 9/1996 | Büttner-Janz | 623/17 |
| 5,609,635 A | 3/1997 | Michelson | 623/17 |
| 5,645,597 A | 7/1997 | Krapiva | 623/17 |
| 5,674,295 A | 10/1997 | Ray et al. | 623/17 |
| 5,674,296 A | 10/1997 | Bryan et al. | 623/17 |
| 5,681,310 A | 10/1997 | Yuan et al. | 606/61 |
| 5,716,416 A | 2/1998 | Lin | 623/17 |
| 5,782,832 A | 7/1998 | Larsen et al. | 606/61 |
| 5,824,093 A | 10/1998 | Ray et al. | 623/17 |

(List continued on next page.)

FOREIGN PATENT DOCUMENTS

EP  0179695  4/1986  ............. A61F/2/44

OTHER PUBLICATIONS

Orion Anterior Cervical Plate System, Danek (Catalog), 1994.

Primary Examiner—Jeffrey A. Smith
(74) Attorney, Agent, or Firm—Emerson & Skeriotis; Roger D. Emerson; John M. Skeriotis

(57) ABSTRACT

A spinal fusion implant and method for maintaining proper lumbar spine curvature and intervertebral disc spacing where a degenerative disc has been removed. The one-piece implant comprises a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopedic screw to be retained entirely within the access passage. A spinal fusion implant embodied in the present invention may be inserted anteriorly or laterally.

20 Claims, 3 Drawing Sheets

U.S. PATENT DOCUMENTS

| | | | |
|---|---|---|---|
| 5,824,094 A | 10/1998 | Serhan et al. | 623/17 |
| 5,827,328 A | 10/1998 | Buttermann | 623/17 |
| 5,843,082 A | 12/1998 | Yuan et al. | 606/61 |
| 5,860,973 A | 1/1999 | Michelson | 606/61 |
| 5,861,041 A | 1/1999 | Tienboon | 623/17 |
| 5,865,846 A | 2/1999 | Bryan et al. | 623/17 |
| 5,865,847 A | 2/1999 | Kohrs et al. | 623/17 |
| 5,865,848 A | 2/1999 | Baker | 623/17 |
| 5,885,287 A | 3/1999 | Bagby | 606/61 |
| 5,888,223 A | 3/1999 | Bray, Jr. | 923/17 |
| 5,888,228 A | 3/1999 | Knothe et al. | 623/17 |
| 5,893,890 A | 4/1999 | Pisharodi | 623/17 |
| 5,895,428 A | 4/1999 | Berry | 623/17 |
| 5,968,098 A | 10/1999 | Winslow | 623/17 |
| 6,066,175 A * | 5/2000 | Henderson et al. | 623/17.11 |

\* cited by examiner

ANTERIOR LUMBAR INTERBODY FUSION IMPLANT AND METHOD FOR FUSING ADJACENT VERTEBRAE

BACKGROUND OF THE INVENTION

This application claims the benefit of U.S. Provisional Application 60/131,900 filed Apr. 30, 1999 by the same inventor, Nathan S. Simpson, entitled ANTERIOR LUMBAR INTERBODY FUSION IMPLANT.

FIELD OF THE INVENTION

This invention relates to interbody spinal fusion implants and surgical procedures for implanting load bearing devices in intervertebral disc spaces after removal of damaged or diseased discs, with the implanted devices being securely connected to the adjacent vertebrae to stabilize the vertebrae while providing for proper transmission of loads therebetween, and being hollow to receive bone graft for fusion of the vertebrae.

More particularly, the present invention relates to interbody spinal fusion implants and a procedure for surgically implanting a device of novel design that 1) has a thickness selected to restore and maintain proper spacing between the end plates of two adjacent vertebrae of the spine, 2) has its top and bottom surfaces inclined to define a wedge shape when viewed in side elevation if such inclination is needed to restore and maintain normal spinal lordosis by restoring and maintaining the normal anatomic angular relationship of the vertebrae, 3) is rigidly connected to each of the adjacent vertebrae by large screws that angle upwardly and downwardly from an anterior or side region of the implant and that thread through the vertebral end plates and into the soft cancellous bone in the central regions of the adjacent vertebrae to prevent relative movement of the adjacent vertebrae, 4) defines a hollow central region for receiving bone graft material for fusing the vertebrae, and 5) provides annular load-carrying portions of the implant that surround the central region and function to transmit loads directly, in a physiologic manner, from the hard cortical periphery of one vertebral end plate to the hard cortical periphery of the adjacent vertebral end plate.

RELATED ART

The vertebrae of the human spine are arranged in a columnar array one atop another, with each horizontally extending space between adjacent pairs of the vertebrae being provided with a separate intervertebral disc that transmits between adjacent vertebrae such forces as are imposed on and carried by the spine, while also functioning to cushion and permit a limited amount of relative movement to take place between the adjacent vertebrae. In a healthy spine, 1) each vertebra is composed of a hard outer ring of cortical bone, and a softer center of cancellous bone; 2) each intervertebral disc is composed of a tough outer ring of fibrous material, and a softer center of jelly-like material; and, 3) the physiologic manner in which loads are carried by the spine makes use of the hard fibrous annuli of the discs to transmit force between the hard cortical periphery of the vertebrae.

The cervical and lumbar areas of the human spine are, in a healthy state, lordotic such that they curve convexly forward. Normal lordosis results, at least in significant measure, from the normal wedge-shaped nature of the spaces between adjacent pairs of the cervical and lumbar vertebrae, and the normal wedge-shaped nature of the intervertebral discs that fill these spaces. If disc damage or degeneration occurs, lordosis tends to be lost, at least in part, because the wedge-shaped character of the discs diminishes and may become lost—hence, the wedge-shaped character of the spaces between adjacent cervical and lumbar vertebrae is likewise caused to diminish, and normal spinal curvature is altered as a result. Moreover, if normal disc thickness diminishes, as is common in the presence of disc damage or disease, the normal spacing between the vertebrae is thereby caused to diminish, causing the height of the spinal column to be undesirably diminished. Loss of lordosis and loss of proper vertebral spacing disturb the overall mechanics of the spine, often causing cascading degenerative changes.

Disc degeneration and the spinal changes that result can bring pain. An accepted treatment for back pain caused by a degenerative disc is to remove the disc and fuse the adjacent vertebrae in a manner that maintains suitable spacing of the vertebrae while preventing the vertebrae from moving relative to each other, for example by filling the intervertebral space where the disc was removed with bone graft that will enable the adjacent vertebrae to grow together and become one solid piece of bone.

The main front (i.e., anterior) portions of adjacent vertebrae between which an intervertebral disc normally resides are referred to by the term "vertebral bodies." The anterior space between adjacent vertebral bodies where a disc normally resides is referred to by the term "intervertebral disc space." When bone graft material that has been inserted into the intervertebral disc space fuses the vertebral bodies of adjacent vertebrae, the process is referred to as "anterior interbody fusion."

Anterior interbody fusion may require weeks, sometimes months to achieve a desirable result, and is likely to achieve unsatisfactory results if relative movement takes place between the adjacent vertebrae while fusion is underway. If relative movement of adjacent vertebral bodies takes place while fusion is underway, this will, as a minimum, slow the rate of fusion, and can prevent acceptable fusion results from being achieved.

Also, if relative movement takes place while fusion is underway, significant continued back pain after surgery may result. To stabilize the adjacent vertebrae and prevent relative movement from taking place, one traditional approach has been to place the patient in a body cast, a procedure that still is used in many instances. To avoid using a body cast and to improve the prospects for achieving satisfactory fusion by more directly immobilizing adjacent vertebrae, some surgeons have used steel rods and other devices that are secured to the posterior of the vertebrae. A significant drawback associated with the use of such posterior appliances is the need for posterior surgery to put them in place.

Operating on the spine from a posterior approach disrupts posterior muscles causing permanent muscle dysfunction, referred to as "fusion disease"—hence, posterior back surgery is to be avoided unless essential. Other drawbacks accompanying the use of such posterior immobilizers include the need for a second surgery to remove these temporary appliances once satisfactory fusion has been achieved, and the discomfort, inconvenience and danger that can result from having to live with this hardware for weeks or months following the original surgery.

While a variety of anterior interbody fusion techniques and implant devices have been developed for use in the cervical region of the spine where the vertebrae are smaller and the loads that must be transmitted between adjacent vertebrae are smaller than in the lumbar region of the spine, it has proven more elusive to achieve consistently good anterior interbody fusion results in the lumbar region of the spine without having to employ body casts or temporary installations of posterior immobilizers.

An approach that has been used with greater success to achieve anterior interbody fusion in the lumbar region of the spine than in the cervical region of the spine has been to install, within an intervertebral space where a degenerative disc has been removed, a pair of so-called "threaded fusion cages." Threaded fusion cages are of generally cylindrical form and are available in a variety of diameters. If threaded fusion cages are to be installed in an intervertebral space from which a degenerated disc has been removed, cages are selected that have sufficiently large diameters to enable their threaded exteriors to "thread" or "bite" into underportions of the vertebral body of the upper vertebra, and into upper portions of the vertebral body of the lower vertebra as each of the cages are "threaded" into the intervertebral space.

After the threaded fusion cages are installed, their hollow interiors are filled with bone graft material so that bone growth will take place within and about the threaded fusion cages while the cages serve to maintain proper spacing between adjacent vertebrae.

While bone growth is taking place, spinal loads are transmitted between the adjacent vertebrae principally by the fusion cages inasmuch as the bone graft material is not capable of participating to a significant degree in carrying compressive force. If bone growth progresses satisfactorily to provide good fusion results, the one-piece bone structure that is formed from the adjacent vertebrae relies principally upon its own integrity and strength to carry spinal loads.

In a number of instances, threaded fusion cages have failed to function in the desired manner to provide needed back pain relief and/or to maintain adequate stability to enable proper fusion results to be achieved. In some instances, threaded fusion cages not only have failed to provide one or both of these basic objectives, but also have been found to cause nerve damage or to present other disadvantages and drawbacks. When unsatisfactory results have been obtained even though accepted procedures for installing threaded fusion cages have been followed, it is believed that one or more of the following explanations may apply:

1) Threaded fusion cages engage very little of the hard peripheral ring of cortical bone of each of two adjacent vertebrae; rather, the fusion cages mainly reside between vertebral regions of soft cancellous bone. Thus, threaded fusion cages rely significantly if not principally on the soft cancellous bone centers of adjacent vertebral bodies to transmit loads between adjacent vertebrae rather than on the hard cortical peripheries of the vertebral bodies which are vastly better suited for this purpose. This reliance on soft rather than hard bone tissue to transmit loads along the spine violates the most basic of orthopedic biomechanical principles, is opposite to the natural state wherein the tough fibrous periphery of an intervertebral disc transmits loads between the hard peripheral bone areas of adjacent vertebral bodies, and unquestionably accounts for some of the complications that are seen when threaded fusion cages subside into vertebral bodies and fusion fails to occur. Furthermore, because the generally cylindrical outer surfaces of the fusion cages engage the end plates of adjacent vertebral bodies along relatively small, relatively narrow areas of engagement, they do not apply the loads carried by the spine to large surface areas of the end plates of the vertebral bodies, but rather tend to apply these loads in a concentrated manner along the narrow regions where they engage the vertebral body end plates, which can cause one or both of the fusion cages installed between two adjacent vertebrae to puncture one of both of the vertebral end plates and subside into the vertebrae.

2) Threaded fusion cages are not rigidly fixed to the adjacent vertebral bodies they engage. Despite the tendency of their threaded exteriors to "bite" into the end plates of adjacent vertebrae, the generally cylindrical character of the fusion cages can permit relative movement of the vertebrae to take place—much as would occur if two elongate metallic "rollers" were inserted between two stacked blocks of wood. The roller-like character of the cages can, and in some instances does, fail to immobilize the adjacent vertebrae, and the unwanted relative movement that may result is disruptive to fusion. Moreover, because the generally cylindrical fusion cages are not rigidly, mechanically attached to the adjacent vertebrae, threaded fusion cages cannot be used where there is preexisting instability of the spine. If spinal instability exists for any reason, the use of threaded fusion cages risks undesirable results.

3) Threaded fusion cages are not anatomically shaped to conform to the intervertebral spaces in which they are installed. Rather, they are of substantially uniform diameter along their lengths, with their diameters being chosen to correspond to the vertical height of the interbody space they are to occupy. What this means is that the wider (or taller) the intervertebral space into which fusion cages are to be threaded, the larger the diameter of cages that must be selected, otherwise their threaded outer surfaces will fail to "bite" into the end plates of each of the adjacent vertebral bodies. In some instances, the pair of threaded fusion cages that are installed side by side in a wide intervertebral space are of a diameter sufficiently large to crowd nerves and/or to put other tissue at risk. Nerve injury has been observed to occur with greater frequency as fusion cages of increasingly greater diameter are utilized. The replacement of a damaged or diseased disc that is especially thick or plump may present a challenge that cannot be suitably addressed through the use of large diameter threaded fusion cages in view of the unacceptable nerve crowding that would result.

4) Threaded fusion cages are not designed to restore and maintain the normal curve of the lumbar spine, known as lordosis. Normal intervertebral discs have something of a "tapered wedge" shape, with the vertebral endplates of adjacent vertebrae defining surfaces that do not normally extend in parallel planes. When discs degenerate and collapse, they cause the spine to lose some of its normal curvature, which disturbs normal biomechanical function, and can lead to further deterioration. Threaded fusion cages do nothing at all to restore and maintain proper lordosis. Rather, threaded fusion cages seek to fix the configuration of the spine with the end plates of adjacent vertebral bodies extending in substantially parallel planes.

5) Nor do threaded fusion cages necessarily function to reestablish proper spacing between adjacent vertebrae. When a collapsed or degenerated disc is removed and threaded fusion cages are inserted to maintain the disc spacing that then exists, the intervertebral disc space may be less than it should be to accommodate the volume or capacity of the spine and perhaps should be widened to more closely reestablish normal physiology—but widening the intervertebral space will require that threaded fusion cages of greater diameter be installed, and the problems that may result with the use of larger diameter cages may be significantly more devastating than will result if the narrowed intervertebral space is maintained, so smaller diameter fusion cages may be selected for use, and the problem of diminished intervertebral disc spacing may be largely ignored.

SUMMARY OF THE INVENTION

The present invention addresses the foregoing and other needs and drawbacks of the prior art by providing an anterior lumbar interbody fusion method and device that can be utilized to restore and maintain proper lumbar spine curvature and proper intervertebral disc spacing, and that transmits spinal loads in a proper physiologic manner through the intervertebral space where a regenerative disc has been removed from the periphery of hard cortical bone of one vertebra directly to the periphery of hard cortical bone of the adjacent vertebra while being rigidly connected to both of the adjacent vertebral bodies to thereby positively prevent relative movement from taking place therebetween, and while providing a hollow central region where bone graft is inserted so that an optimal environment is provided anterior lumbar interbody fusion to take place in a minimum of time and with good results.

In accordance with the invention, there is provided a one-piece implant that is shaped roughly the same as a normal disc.

According to another aspect of the invention, there are provided implants that are of different left-to-right and front-to-rear sizes for use between vertebral bodies of different sizes.

According to another aspect of the invention, there are provided implants that differ in bottom-to- top thickness.

According to another aspect of the invention, there is provided means for varying the degrees of wedge inclination between the planes of the top and bottom surfaces of the implants.

According to another aspect of the invention, the implant is rigidly coupled to the adjacent vertebral bodies through the use of relatively large screws of a proven orthopedic design.

According to another aspect of the invention, the implant defines a pair of inclined screw passages that are accessible either anteriorally or laterally for guiding threaded screws through the end plates of adjacent vertebral bodies to assist in ensuring that the screws are installed at proper angles of inclination to form effective connections with the adjacent vertebrae.

According to another aspect of the invention, there is provided a countersunk shoulder at the entryway of the screw passages for reception of the screw heads.

According to another aspect of the invention, the implant is generally annular in shape comprising a peripheral ring of rigid material that surrounds a hollow central area. The rigid periphery fits directly between the hard cortical peripheral rings of the adjacent peripheral bodies, but does nothing to crowd adjacent nerves or other tissue.

According to another aspect of the invention, the implant includes a relatively large open central region that can accommodate a sizable volume of bone graft material, wherein the rigid periphery of the implant serves as a protective fence that guards the region where bone growth takes place as fusion is underway.

One advantage of the invention, is provided by the more natural shape of the implant and the fact that it preferably is a one-piece, integral structure. The implant is therefore easier to insert and to properly position in an intervertebral space than two fusion cages which typically require the use of rotary tools to drill selected locations and to rotate the cages to thread them into the intervertebral space under flouroscopic guidance and with an exceedingly small margin for error. Accurate cage placement is quite essential; perfecting the technique to effect proper cage placement is difficult; and, the need for constant flouroscopic imaging exposes the patient to a high dose of radiation. By contrast, implants embodying the preferred practice of the present invention are easier to place, more forgiving of technique, and require only intermittent X-ray images to effect satisfactory placement.

Another advantage of the invention is that the implant can be used in many situations where there is preexisting instability of the spine inasmuch as the preferred form of implant takes much the same shape as a healthy disc and is rigidly connected by screws to the adjacent vertebral bodies.

Another advantage of the present invention is the provision of an implant that can be selected of proper size and thickness to appropriately maintain proper intervertebral spacing, with its hard peripheral regions being properly positioned to transmit spinal loads directly between the hard cortical peripheries of the adjacent vertebral bodies. Moreover, an implant can be selected to conform the intervertebral space to an appropriate wedge shape and to maintain proper spacing between the adjacent vertebral bodies so that proper spinal lordosis is reestablished and/or maintained, and so that the height of the spinal column is not inappropriately shortened.

Another advantage of the invention is that use of the large screws reliably immobilizes the vertebrae in relation to each other to provide an optimum environment within which good fusion results are likely to be received. Also, by eliminating relative movement of the vertebrae to be fused, instances of continuing back pain following surgery are significantly diminished, thereby enhancing the comfort of the patient especially during the higher risk time while the fusion process is underway.

Another advantage of the invention is that when screws are installed and tightened in place to seat their enlarged heads against the countersunk shoulders provided at the entryways of these passages, reliably rigid connections are established between the implant and the adjacent vertebral bodies. Providing countersunk or recessed openings to receive the heads of the screws is of particular importance when the screws are installed anteriorly (as opposed to laterally, from the left and/or right) to prevent the screw heads from projecting into engagement with adjacent vessels (e.g., the inferior vena cava and the aorta).

Another advantage of the invention is that the need to replace an especially thick or plump damaged or diseased disc does not bring with it nerve crowding problems such as are encountered where a pair of large diameter threaded screw cages are inserted into a thick intervertebral space.

Another advantage of the invention is the ability to utilize a sizable quantity of bone graft material and the protective central positioning of a majority of the bone graft material between the soft cancellous regions of the adjacent vertebral bodies provides a truly optimal environment for rapid and proper bone growth—so that good fusion results tend to be obtained within a minimum of time.

In the detailed discussion that follows, other features and advantages also will become apparent. For example, two implant embodiments are disclosed, one that is intended to be installed from the front of the spine (i.e., anteriorally), and one that is designed to be inserted from the side of the spine (i.e., laterally). While the anterior version of the implant preferably provides an access opening through the anterior side wall of the implant for inserting bone graft, the lateral version of the implant preferably provides at least one access opening through at least one of the lateral side walls of the implant for inserting bone graft.

Other improved features are contemplated, including a more complex form of the implant that provides a capability to telescope to adjust its thickness and perhaps also its wedge-shaped character as it is being inserted and positioned in an intervertebral space—features that are likely to render the implant even more suitable to install utilizing techniques of minimally invasive surgery (surgery that typically utilizes a video endoscope).

Also contemplated by the invention is a preferred method for replacing a degenerated intervertebral disc and fusing the adjacent vertebrae utilizing a novel interbody implant device of the type described above that preferably is sized, configured, positioned and secured in the manner described above to provide the advantages and features described above—advantages and features that permit the implant to be used with improved success and safety to achieve good results more consistently than presently is the case with the use of threaded fusion cages or other forms of implants and surgical techniques.

BRIEF DESCRIPTION OF THE DRAWINGS

These and other features, and a fuller understanding of the present invention may be had by referring to the following description and claims, taken in conjunction with the accompanying drawings, wherein:

DESCRIPTION OF THE PREFERRED EMBODIMENT

Figure 1:
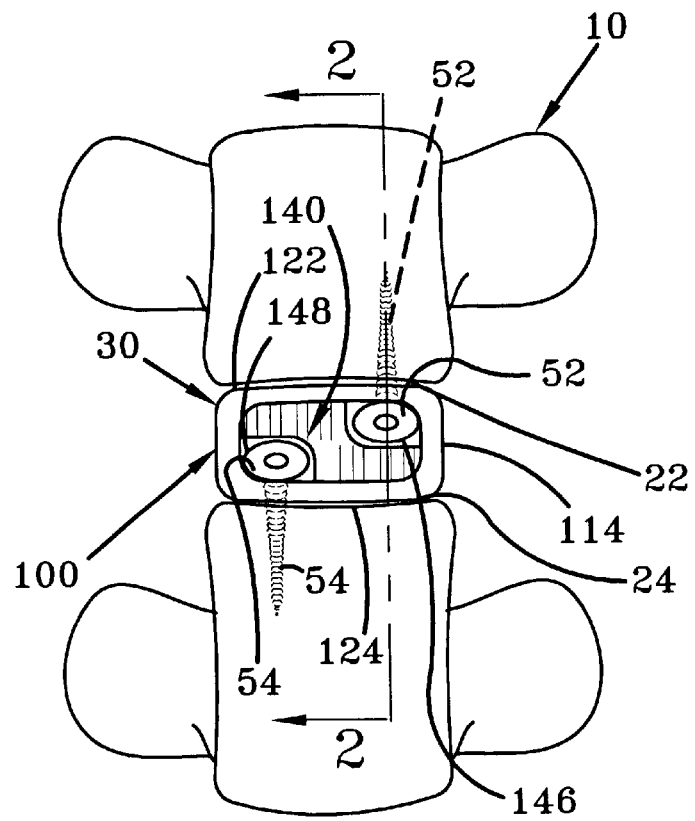
FIG. 1 is a front or anterior elevational view of a first embodiment of an interbody implant between two vertebrae.
Figure 2:
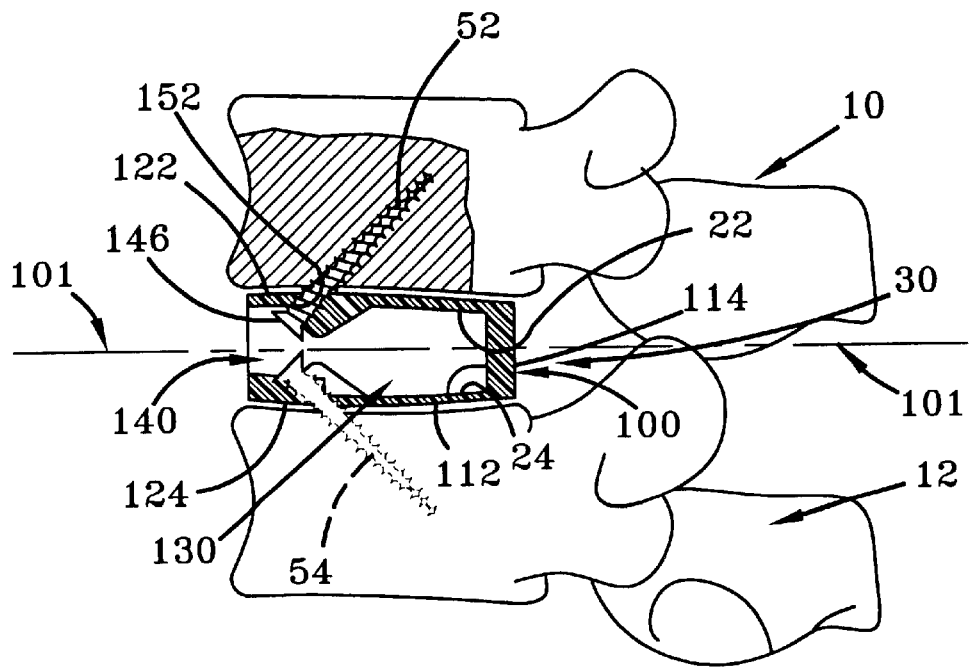
FIG. 2 is a side elevational view thereof, with portions broken away to a plane by a line 2—2 in FIG. 1.

Referring to FIGS. 1 and 2, two adjacent vertebrae of the human spine are indicated generally by the numerals 10 and 12. The vertebrae 10, 12 have endplates 22, 24, respectively, that define opposite ends of an intervertebral space 30. The intervertebral space 30 narrows from its anterior toward its posterior (i.e., from left to right as viewed in FIG. 2 in a wedge-shaped manner, as is typically found in the lumbar region of a healthy human spine having normal lordosis.

Inserted between the endplates 22, 24 is a first form of implant that embodies features of the preferred practice of the present invention, indicated generally by the numeral 100. The implant 100 preferably is formed of titanium or other appropriately rigid and inert material, and is held in place by orthopedic screws 52, 54 that also are preferably formed of titanium or other appropriately rigid and inert material.

Figure 3:
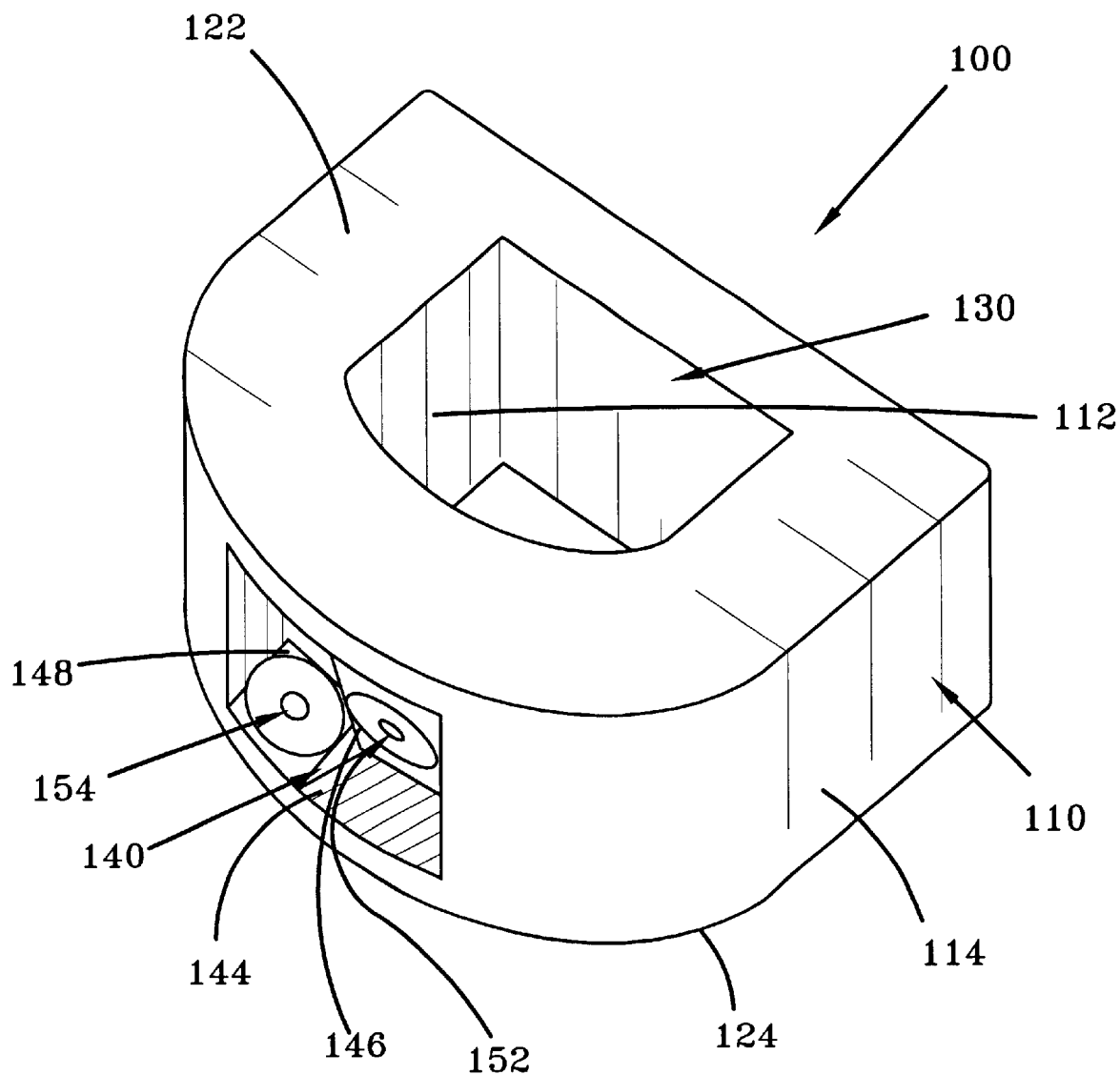
FIG. 3 is a perspective view, on an enlarged scale, of the implant embodiment of FIGS. 1 and 2; and, FIG. 4 is a perspective view of a second embodiment of interbody implant.

Referring to FIG. 3, the implant 100 has a generally annular body 110 that defines substantially continuous interior and exterior surfaces 112, 114 that extend between and connect the interior and exterior peripheries of a pair of opposed annular end surfaces 122, 124. The opposed annular end surfaces or walls 122, 124 are configured to engage hard cortical peripheral portions of the endplates 22, 24. The interior surface 112 surrounds an interior chamber 130 that can be filled with bone graft material (not shown) for extending between and effecting fusion of central cancellous portions of the endplates 22, 24. The exterior surface 114 gives the body 110 a configuration that is adapted to be received within the intervertebral space 30 between the vertebral endplates 22, 24 at substantially the same position as would be occupied by a healthy intervertebral disc (not shown).

Referring again to FIG. 2, an access passage 140 has a posterior end region 142 that opens through the interior surface 112, and an anterior end region 144 that opens through the exterior surface 114. The passage 140 provides access to the interior chamber 130 to permit bone graft material (not shown) to be packed into the interior chamber 130 after the implant 100 has been affixed in proper position by means of the orthopedic screws 52, 54.

Referring to FIGS. 1 and 3, located within the access passage 140 and facing generally toward the anterior end region 144 of the passage 140 are a pair of inclined surfaces 146, 148. Referring to FIG. 3, countersunk screw-receiving passages 152, 154 open through the inclined surfaces 146, 148, with their enlarged countersunk end regions facing generally toward the anterior end region 144 of the passage.

The screw-receiving passages 152, 154 are inclined, preferably at about forty-five degree angles relative to an imaginary centerplane that extends centrally through the implant 100 (indicated in FIG. 2 by the numeral 101), so that, when the orthopedic screws 52, 54 are installed in the passages 152, 154, the enlarged heads of the screws are seated in the countersunk or recessed end regions of the screw-receiving passages 152, 154. When the implant 100 is properly positioned, the screw 52 angles upwardly into the central cancellous bone region of the vertebra 10, and the screw 54 angles downwardly into the central cancellous bone region of the vertebra 12 to rigidly anchor the implant 100 to the vertebrae 10, 12. The anchoring of the implant 100 to the vertebrae 10, 12 by the screws 52, 54 holds the implant 100 in proper position and immobilizes the vertebrae 10, 12 to prevent their moving relative to each other so that an optimum environment for growth of bone graft and eventual fusion of the vertebrae 10, 12 can take place. These screws 52, 54 are specifically placed to resist motion in six degrees of freedom. The seating of the screw heads within the recessed outer end regions of the screw-receiving passages 152, 154 ensures that the screw heads do not project into engagement with vessels and tissues located adjacent the exterior surface 114.

Figure 4:
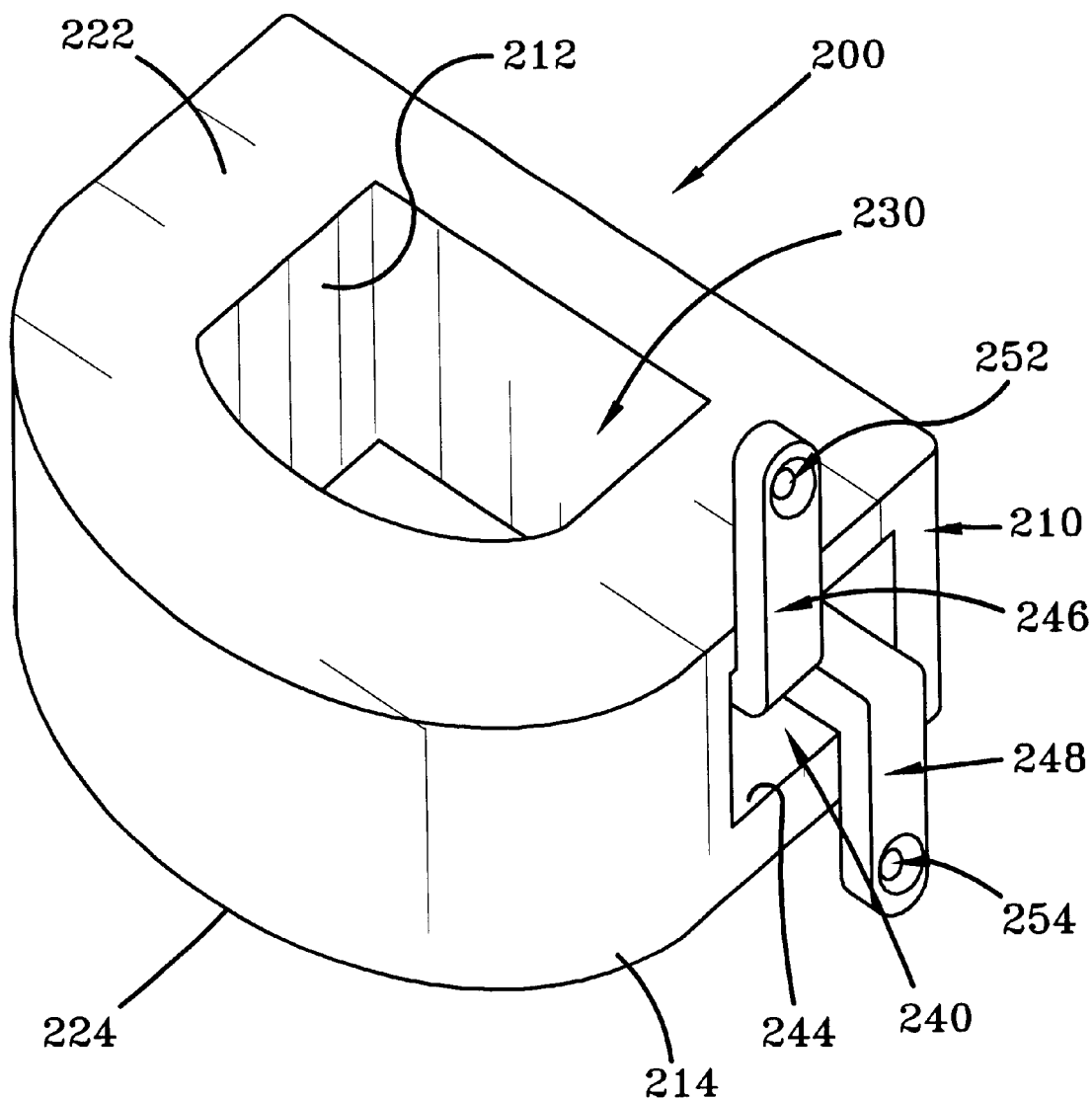

The implant embodiment 100 as shown in FIGS. 1–3 is intended to be inserted anteriorally—and, for this reason, its access passage 140 and its screw-receiving passages 152, 154 face anteriorally. If lateral insertion is preferred, the implant embodiment 200 depicted in FIG. 4 is provided. Referring to FIG. 4, the implant 200 has a generally annular body 210 that defines substantially continuous interior and exterior surfaces 212, 214 that extend between and connect the interior and exterior peripheries of a pair of opposed annular end surfaces 222, 224. The opposed annular end surfaces or walls 222, 224 are configured to engage hard cortical peripheral portions of the endplates 22, 24 (not shown in FIG. 4, but seen in FIGS. 1 and 2). The interior surface 212 surrounds an interior chamber 230 that can be filled with bone graft material (not shown) for extending between and effecting fusion of central cancellous portions of the endplates 22, 24. The exterior surface 214 gives the body 210 a configuration that is adapted to be received within the intervertebral space 30 between the vertebral endplates 22, 24 at substantially the same position as would be occupied by a healthy intervertebral disc (not shown). An access passage 240 has an inner end region (not shown) that opens through the interior surface 212, and an outer end region 244 that opens through the exterior surface 214. The passage 240 provides access to the interior chamber 230 to permit bone graft material (not shown) to be packed into the interior chamber 230 after the implant 200 has been affixed in proper position by means of the orthopedic screws 52, 54 (not shown in FIG. 4, but seen in FIGS. 1 and 2).

Defined near the outer end region of the access passage 240 are a pair of oppositely extending tab-like formations 246, 248. Countersunk screw-receiving passages 252, 254 are formed through the tab-like formations 246, 248, with their enlarged countersunk end regions facing toward the same side of the implant 200 as the access passage 240. The screw-receiving passages 252, 254 are inclined, preferably at about thirty to about forty-five degree angles relative to an imaginary centerplane (not shown) that extends centrally through the implant 200 (in the same manner that the center plane 101 extends centrally through the implant 100, as depicted in FIG. 2), so that, when the orthopedic screws 52, 54 are installed in the passages 252, 254 (with their enlarged heads seated in the countersunk end regions of the screw-receiving passages 252, 254), the screw 52 angles upwardly through the outer periphery of cortical bone and into the central cancellous bone region of the vertebra 10, and the screw 54 angles downwardly through the outer periphery of cortical bone and into the central cancellous bone region of the vertebra 12 to rigidly anchor the implant 200 to the vertebrae 10, 12. The anchoring of the implant 200 to the vertebrae 10, 12 by the screws 52, 54 holds the implant 200 in proper position and immobilizes the vertebrae 10, 12 to prevent their moving relative to each other so that an optimum environment for growth of bone graft and eventual fusion of the vertebrae 10, 12 can take place.

As those who are skilled in the art will readily appreciate, the provision of the depicted tab-like formations 246, 248 on the implant 200 shows one of a number of alternate ways in which orthopedic screws, such as the screws 52, 54, can connect with an interbody fusion implant. The approach of providing inclined surfaces 146, 148 within an access passage 140, such as is used with the implant embodiment 100, also can be used with the implant embodiment 200. The approach of positioning the enlarged head end regions of orthopedic screws within an access passage is preferred in many instances because it eliminates the need for tab-like formations or other structure to extend out of the intervertebral space and/or along-side one or both of the adjacent vertebrae that are to be fused, thus protecting visceral structures.

The orthopedic screws 52, 54 that presently are preferred for use with the implant embodiments 100, 200 are 8.0 mm screws that have threads configured for good retention in soft cancellous bone after suitable holes (not shown) have been drilled and tapped. Screws of this type are widely available from a variety of suppliers of medical appliances; and, inasmuch as the development of orthopedic fasteners is an active art, it clearly is within the scope of the present invention to utilize new and improved forms of orthopedic screws and other types of improved orthopedic fasteners and fastening systems as they are developed and are shown to be effective in providing good service longevity.

In preferred practice, the implants 100, 200 are provided in a variety of sizes and thicknesses, and may also be provided with a variety of angles of inclination between the planes of their pairs of opposed end surfaces 122, 124 and 222, 224. Thicknesses (measured as the distance between the planes of the opposed end surfaces 122, 124, or 222, 224 at central locations of the implants 100, 200) of about 12.0 mm to about 20.0 mm, in increments of about 2.0 mm are presently preferred.

Left-to-right widths of about 30.0 mm to about 60.0 mm in increments of about 5.0 mm are presently preferred, as are anterior-to-posterior widths of about 30.0 mm to about 40.0 mm in increments of about 5.0 mm.

Alternatively, an optimized range of sizes of implants can be provided that includes a "large" size implant having a left-to-right width of about 60.0 mm and an anterior-to-posterior width of about 40.0 mm, a "small" size implant having a left-to-right width of about 30.0 mm and an anterior-to-posterior width of about 30.0 mm, with other "inbetween" sizes within the ranges set out just above, and with each of these sizes being provided in a range of thicknesses of about 12.0 mm to about 20.0 mm, in increments of about 2.0 mm.

As those who are skilled in the art will readily understand, the sizes stated are "preferred," which does not exclude the use of other sizes, including other sizes that are larger and smaller than those enumerated here.

Inasmuch as new biocompatible materials having the strength and rigidity (and other implant-appropriate characteristics well known to those who are skilled in the art) are always under development, it is clear that titanium and various types of biomaterials that typically are used to form implants today may be replaced by other more advantageous materials tomorrow.

It will therefore be understood that implants embodying the preferred practice of the present invention may be formed from a wide variety of biocompatible materials designed to be incorporated into the host's normal tissue, such as polyglycolic acid, regardless of whether these materials exist or are available for present-day use, without departing from the spirit and scope of the invention.

As those who are skilled in the art will understand, the surgery required to replace a diseased or damaged disc with an interbody implant that embodies the preferred practice of the present invention utilizes the usual anterior retroperitoneal approach to the spine, with the great vessels being mobilized and protected in the usual manner. The annulus is sharply incised anteriorly to allow a complete discectomy to be performed. The entire disc is removed except for the outermost portions of the lateral and posterior annulus.

The endplates of the vertebrae are carefully scraped clean of all disc material. The height and width of the disc space are measured, and the correct size trial implant is chosen and inserted. X-ray imaging is then used to confirm correct placement and size of the implant.

The trial implant is then removed, and the final implant is inserted and its position checked in the same manner. The vertebral bodies are drilled and tapped, and screws are inserted while the implant is held firmly in proper position. Bone graft is packed into the implant which is covered with cellulose gauze. A final check using X-rays is made to confirm that the implant still is in its proper position, and the abdomen is closed in the usual manner.

If a lateral approach is employed, the technique differs only in that, after making the standard lateral retroperitoneal approach to the spine, the disc is incised laterally and removed entirely except for the most peripheral portions of the contralateral, anterior, and posterior annulus.

Included among the features of the invention that believed to be novel and entitled to protection, and claimed herewith, is the provision and use of an interbody spinal fusion implant (for being inserted between the vertebral endplates of two adjacent vertebrae in the human spine for fusion of the two adjacent vertebrae) comprised of a rigid, unitary annular member having structural means for defining an annular body 1) having a pair of opposed annular end walls for engaging hard cortical peripheral portions of the endplates, 2) having a substantially continuous interior wall extending transversely between and connecting inner peripheries of the opposed annular end walls for surrounding an interior chamber that can be filled with bone graft material for extending between and effecting fusion of softer cancellous portions of the end-plates, 3) having a substantially continuous exterior wall extending transversely between and connecting outer peripheries of the opposed annular end walls for defining an exterior configuration of the member that is adapted to be received within the intervertebral space between the vertebral endplates at substantially the same position as would be occupied by a healthy intervertebral disc, 4) having an access passage that opens at opposite ends through the interior and exterior walls for providing access to the interior chamber to permit bone graft material to be packed into the interior chamber, and 5) having screw-receiving passages formed through the member for receiving head-end portions of at least one threaded, headed orthopedic screw that extends in an inclined manner through one of the screw-receiving passages and through the cancellous portion of the endplate of one of the adjacent vertebrae to rigidly anchor the implant to said one of the adjacent vertebrae, and for receiving head-end portions of at least one other threaded, headed orthopedic screw that extends in an inclined manner through another of the screw-receiving passages and through the cancellous portion of the endplate of the other of the adjacent vertebrae to rigidly anchor the implant to said other of the adjacent vertebrae.

Also believed to be novel and entitled to protection is the provision of an implant of the type described just above 1) having its opposed annular end walls extending substantially in planes that are inclined relative to each other at an angle selected to at least partially restore normal lordosis of the spine by positioning the endplates of the two adjacent vertebrae to extend at substantially the normal angle of inclination that would be found in a healthy human spine, 2) having the configuration defined by the exterior wall defining an implant size that is selected in accordance with the size of the two adjacent vertebrae so that the opposed annular end walls will engage sizable surface areas of the hard cortical peripheries of the endplates of the two adjacent vertebrae for transferring spinal loads directly therebetween, and 3) having an implant height or thickness (measured between the opposed annular end walls) that is selected to correspond to an appropriate spacing to be maintained between the endplates of the two adjacent vertebrae.

Also believed to be novel and entitled to protection are such additional features as providing the implant in an anterior-insertion form with its access passage and its screw-receiving passages being accessible from an anterior side of the implant, and providing the implant in a lateral-insertion form with its access passage and its screw-receiving passages being accessible from at least a selected left or right side of the implant.

Also believed to be novel and entitled to protection are such methods of fusing two adjacent vertebrae of the human spine as initialized by the insertion between the endplates of the adjacent vertebrae and the affixation to the adjacent vertebrae by orthopedic screws of an interbody spinal fusion implant of the type described, offering various combinations of the features described.

While the invention has been described with a certain degree of particularity, it will be understood that the present disclosure of the preferred embodiment has been made only by way of example, and that numerous changes in the details of construction and the combination and arrangement of elements can be resorted to without departing from the true spirit and scope of the invention.

Having thus described the invention, it is now claimed:

1. An interbody spinal fusion implant adapted for insertion between adjacent vertebrae having spaced endplates that define opposite ends of an intervertebral space, the implant comprising:

a generally hollow annular body defining substantially continuous interior and exterior surfaces extending between opposed annular first and second end surfaces, the interior surface defining an interior chamber, the body having an access passage formed therein extending between the interior and exterior surfaces and communicating with the interior chamber;

first means adapted for receiving an associated first screw into a first screw-receiving passage formed therein and being disposed at a first angle between 30° and 45°, inclusive, to a central plane, the first screw-receiving means comprising a first protrusion extending into the access passage, the first protrusion including a first inclined surface generally facing toward the exterior surface wherein the first inclined surface is generally normal to the first screw-receiving passage; and, second means adapted for receiving an associated second screw into a second screw-receiving passage formed therein and being disposed at a second angle between 30° and 45°, inclusive, to the central plane, wherein the second angle is oppositely inclined relative to the first angle.

2. The interbody spinal fusion implant of claim 1 wherein the first screw-receiving passage includes means adapted for retaining a head of the associated first screw within the access passage.

3. The interbody spinal fusion implant of claim 1 wherein the second screw-receiving means comprises:

a second protrusion extending into the access passage, the second protrusion including a second inclined surface generally facing toward the exterior surface wherein the second inclined surface is generally normal to the second screw-receiving passage.

4. The interbody spinal fusion implant of claim 1 wherein the body has a straight portion and a curved portion whereby the end surfaces are generally D-shaped.

5. The interbody spinal fusion implant of claim 4 wherein the distance between the interior and exterior surfaces is generally greater in the curved portion than the distance between the interior and exterior surfaces in the straight portion.

6. The interbody spinal fusion implant of claim 4 wherein the access passage is formed in the curved portion and is disposed generally perpendicular to the straight portion.

7. The interbody spinal fusion implant of claim 4 wherein the access passage is formed in the curved portion and is disposed generally parallel to the straight portion.

8. The interbody spinal fusion implant of claim 1 wherein the first screw-receiving passage includes a countersunk end region.

9. The interbody spinal fusion implant of claim 8 wherein the second screw-receiving passage includes a countersunk end region.

10. The interbody spinal fusion implant of claim 1 wherein the first end surface lies generally in a first plane which is inclined with respect to the central plane and wherein the second end surface lies generally in a second plane which is inclined with respect to the central plane and wherein the first and second planes are generally converging in a front to back direction.

11. The interbody spinal fusion implant of claim 1 wherein the body has a lateral width of between about 30.0 mm and about 60.0 mm.

12. The interbody spinal fusion implant of claim 1 wherein the body has a front to back width of between about 30.0 mm and about 60.0 mm.

13. The interbody spinal fusion implant of claim 1 wherein the body has a thickness as measured as the distance between the first and second end surfaces at a central location of between about 12.0 mm to about 20.0 mm.

14. The interbody spinal fusion implant of claim 1 wherein the body is formed of a rigid and inert material.

15. The interbody spinal fusion implant of claim 14 wherein the rigid and inert material is titanium or an alloy thereof.

16. A method for fusing adjacent vertebrae having spaced endplates defining opposite ends of an intervertebral space utilizing an interbody spinal fusion implant, first and second orthopedic screws, and bone graft material, the method comprising the steps of:

providing an interbody spinal fusion implant comprising a generally hollow annular body defining substantially continuous interior and exterior surfaces extending between opposed annular first and second end surfaces, the interior surface defining an interior chamber, the body having an access passage formed therein extending between the interior and exterior surfaces and communicating with the interior chamber; first means adapted for receiving a first associated screw into a first screw-receiving passage formed therein and being disposed at a first angle between 30° and 45°, inclusive, to a central plane, the first screw receiving means comprising a first protrusion extending into the access passage, the first protrusion including a first inclined surface generally facing toward the exterior surface wherein the first inclined surface is generally normal to the first screw-receiving passage; and, second means adapted for receiving a second associated screw into a second screw-receiving passage formed therein and being disposed at a second angle between 30° and 45°, inclusive, to the central plane, wherein the second angle is oppositely inclined relative to the first angle;

positioning the interbody spinal fusion implant so that the first end surface engages the endplate of one of the vertebrae and the second end surface engages the endplate of the other vertebrae;

affixing the interbody spinal fusion implant to the vertebrae by installing a first orthopedic screw through the first screw-receiving passage and into a central cancellous bone region of one of the vertebrae and retaining a head of the first orthopedic screw entirely within the access passage, and installing a second orthopedic screw through the second screw-receiving passage and into a central cancellous bone region of the other vertebrae; and, inserting bone graft material through the access passage into the internal chamber in an amount sufficient to extend between the spaced endplates after the step of affixing the interbody spinal fusion implant.

17. The method of claim 16 further comprising the steps of:

inserting a trial implant into the intervertebral space;

utilizing x-ray imaging after the trial implant is inserted to determine correct size and placement of the trial implant; and removing the trial implant before the step of positioning the interbody spinal fusion implant.

18. The method of claim 16 wherein the step of positioning the interbody spinal fusion implant further includes:

inserting the interbody spinal fusion implant anteriorially into the intervertebral space.

19. The method of claim 16 wherein the step of positioning the interbody spinal fusion implant further includes:

inserting the interbody spinal fusion implant laterally into the intervertebral space.

20. The method of claim 16 wherein the step of positioning the interbody spinal fusion implant further includes:

restoring the lordosis of a normal human spine.

* * * * *